United States Patent
Rizk et al.

(10) Patent No.: US 8,865,147 B2
(45) Date of Patent: Oct. 21, 2014

(54) HAIR CLEANSING AND CONDITIONING COMPOSITION

(75) Inventors: Kirolos Rizk, Helmetta, NJ (US); Jaimie Mecca, Clifton, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/460,176

(22) Filed: Apr. 30, 2012

(65) Prior Publication Data

US 2013/0284198 A1    Oct. 31, 2013

(51) Int. Cl.
*A61Q 5/02* (2006.01)
*A61Q 5/12* (2006.01)

(52) U.S. Cl.
USPC .................. 424/70.19; 424/70.11; 424/70.22; 424/70.28

(58) Field of Classification Search
None
See application file for complete search history.

(56) References Cited

U.S. PATENT DOCUMENTS

| | | | |
|---|---|---|---|
| 5,490,955 | A | 2/1996 | Hagan et al. |
| 6,113,892 | A * | 9/2000 | Newell et al. .............. 424/70.19 |
| 6,627,183 | B1 | 9/2003 | Young et al. |
| 6,635,702 | B1 | 10/2003 | Schmucker-Castner et al. |
| 2006/0135392 | A1 | 6/2006 | Ribery et al. |

FOREIGN PATENT DOCUMENTS

| | | | |
|---|---|---|---|
| EP | 2116226 | * | 11/2009 |
| WO | WO-2009135683 A1 | | 11/2009 |

OTHER PUBLICATIONS

Notification of Transmittal of the International Search Report and the Written Opinion of the International Searching Authority, or the Declaration; International Search Report; Written Opinion of the International Searching Authority, International Application No. PCT/US2013/038150.

* cited by examiner

*Primary Examiner* — Jyothsna Venkat
(74) *Attorney, Agent, or Firm* — Novak Druce Connolly Bove + Quigg LLP

(57) ABSTRACT

The present invention comprises a composition for hair cleansing and conditioning, including at least one anionic surfactant, at least one cationic hair conditioning agent, and an acrylate-based polymer capable of thickening and stabilizing the composition, wherein the composition is essentially free of sulfate-based surfactant and silicone-based hair conditioning agent. In addition, the invention also comprises a method of cleansing and conditioning hair by providing a composition having at least one anionic surfactant, at least one cationic hair conditioning agent, and an acrylate-based polymer capable of thickening and stabilizing the composition, applying the composition to treat the hair of a user and rinsing the treated hair with sufficient amount of water.

3 Claims, No Drawings

HAIR CLEANSING AND CONDITIONING COMPOSITION

BACKGROUND OF THE INVENTION

Hair shampoo and conditioner formulations, when applied separately, result in less than desirable results for the user. For instance, after an application of the shampoo, the hair may become too dry. After an application of the conditioner, the hair may become overly conditioned.

Shampoo formulations often contain surfactants such as sodium lauryl sulfate, sodium laureth sulfate, and ammonium laureth sulfate. These sulfate-based surfactants facilitate the cleansing process by decreasing: the surface tension of water and thus allowing water to adhere to the dirt on the hair. However, sulfate-based surfactants have a tendency of making the hair too dry and therefore, consumers prefer to use sulfate-free surfactants as shampoos. There is a need to provide consumers with shampoo products that are free of sulfate-based surfactants.

Hair conditioners contain polydimethylsiloxanes, commonly known as silicones, as part of the formulations. These silicone-based hair conditioning agents, such as dimethicone and cyclodimethicone, have been popular as hair conditioners because they are useful in making hair look full, shiny, smooth and easy to comb. However, upon prolonged usage, silicone-based conditioning agents may form a coating on the hair, thus preventing the hair from getting sufficient moisture. Therefore, despite their apparent effects in making hair look full and shiny, conditioning formulations that contain silicon-based conditioning agents raise concerns among consumers.

Even when shampoo and conditioner formulations are applied at the same time as a mixture, the above-noted problems may not be much alleviated. For instance, the classical 2-in-1 shampoo formulations add a silicone-based conditioner and a suspending agent to a sulfate-based shampoo. However, these 2-in-1 formulations would still not resolve the issues because, as part of the shampoo-conditioner mixture, the shampoo prevents the conditioner from properly conditioning a portion of the hair, while the conditioner prevents the shampoo from properly cleansing another portion of the hair. Furthermore, the components in many of these 2-in-1 formulations contain sulfate-based surfactants and silicone-based conditioning agents.

Therefore, there remains a need for a hair cleansing and conditioning composition that offers a balance between cleansing and conditioning properties while the composition is free of sulfate-based surfactant and silicone-based hair conditioning agent.

BRIEF SUMMARY OF THE INVENTION

According to an embodiment of the invention, a composition for hair cleansing and conditioning includes at least one anionic surfactant; at least one cationic hair conditioning agent; and an acrylate-based polymer capable of thickening and stabilizing the composition, such that the composition is essentially free of sulfate-based surfactant and silicone-based hair conditioning agent.

According to an embodiment of the invention, the at least one anionic surfactant is a member selected from the group consisting of an isethionate, a taurate, a sarcosinate, a sulfosuccinate, a sulfoacetate, a glycinate, a glutamate and a carboxylate, wherein the at least one anionic surfactant has an alkyl chain from $C_8$ to $C_{20}$, and a solubilizing counter cation selected from sodium, potassium and ammonium.

According to an embodiment of the invention, the at least one anionic surfactant is selected from a taurate and an isethionate, wherein the at least one anionic surfactant has an alkyl chain from $C_8$ to $C_{20}$, and a solubilizing counter cation selected from sodium, potassium and ammonium.

According to an embodiment of the invention, the at least one anionic surfactant is a member selected from the consisting of sodium methyl cocoyl taurate, sodium cocoyl isethionate, sodium lauryl methyl isethionate and sodium methyl oleoyl taurate.

According to an embodiment of the invention, the anionic surfactants are two members selected from the group consisting of sodium methyl cocoyl taurate, sodium cocoyl isethionate, sodium lauryl methyl isethionate and sodium methyl oleoyl taurate.

According to an embodiment of the invention, the anionic surfactants are sodium methyl cocoyl taurate and sodium cocoyl isethionate.

According to an embodiment of the invention, the anionic surfactant ranges from about 0.1% to about 16.0% by weight, preferably from about 0.5% to about 14.0% by weight, and more preferably from about 1.0% to about 12.0% by weight, based on the total weight of the composition.

According to an embodiment of the invention, the anionic surfactants are a taurate and an isethionate, wherein the taurate ranges from about 0.1% to about 8.0% by weight, and the isethionate ranges from about 0.1% to about 8.0% by weight; preferably the taurate ranges from about 0.5% to about 7.0% by weight, and the isethionate ranges from about 0.5% to about 7.0% by weight; and more preferably the taurate ranges from about 1.0% to about 6.0% by weight, and the isethionate ranges from about 1.0% to about 6.0% by weight, wherein the weight percentages are based on the total weight of the total composition.

According to an embodiment of the invention, the at least one cationic conditioning agent is a member selected from the group consisting of polyquaterium-10, cetrimonium chloride, behentrimonium chloride, behentrimonium methosulfate, steartrimonium chloride, stearalkonium chloride and dicetyldimonium chloride.

According to an embodiment of the invention, the cationic conditioning agents are two members selected from the group consisting of polyquaterium-10, cetrimonium chloride, behentrimonium chloride, behentrimonium methosulfate, steartrimonium chloride, stearalkonium chloride and dicetyldimonium chloride.

According to an embodiment of the invention, the cationic conditioning agents are polyquaterium-10 and at least one additional cationic hair conditioning agent selected from the consisting of cetrimonium chloride, behentrimonium chloride, behentrimonium methosulfate, steartrimonium chloride, stearalkonium chloride and dicetyldimonium chloride.

According to an embodiment of the invention, the cationic condition agents are polyquaterium-10 and cetrimonium chloride.

According to an embodiment of the invention, the cationic hair conditioning agent ranges from about 0.05% to about 7.0% by weight, preferably from about 0.1% to about 5.5% by weight, and more preferably from about 0.2% to about 4.0% by weight, based on the total weight of the composition.

According to an embodiment of the invention, polyquaterium-1.0 ranges from about 0.05% to about 2.0% by weight, and the at least one additional cationic hair conditioning agent ranges from about 0.1% to about 5.0% by weight; preferably polyquaterium-10 ranges from about 0.1% to about 1.5% by weight, and the at least one additional cationic hair conditioning agent ranges from about 0.25% to about 4.0% by weight;

and more preferably polyquaterium-10 ranges from about 0.2% to about 1.0% by weight, and the at least one additional cationic hair conditioning agent ranges from about 0.4% to about 3.0% by weight, wherein the weight percentages are based on the total weight of the composition.

According to an embodiment of the invention, the acrylate-based polymer is a member selected from the group consisting of polyacrylate-1 crosspolymer, carbomer, acrylates/C10-30 alkyl acrylate crosspolymer, acrylates/acrylamide copolymer and acrylate copolymer.

According to an embodiment of the invention, the acrylate-based polymer is an acrylates/C10-30 alkyl acrylate crosspolymer.

According to an embodiment of the invention, the acrylate-based polymer ranges from about 0.05% to about 2.0% by weight; preferably from 0.1% to about 1.5% by weight; and more preferably from 0.2% to about 1.0% by weight, based on the total weight of the composition.

According to an embodiment of the invention, the anionic surfactants are sodium methyl taurate and sodium cocoyl isethionate, the cationic conditioning agents are polyquaterium-10 and cetrimonium chloride, and the acrylate-based polymer is an acrylates/C10-30 alkyl acrylate crosspolymer.

According to an embodiment of the invention, the at least one anionic surfactant ranges from about 0.1% to about 16% by weight, the at least one cationic hair conditioning agent ranges from about 0.05% to about 7.0% by weight, and the acrylate-based polymer ranges from 0.05% to about 2.0% by weight, wherein the weight percentages are based on the total weight of the composition.

According to an embodiment of the invention, the composition comprises sodium methyl cocoyl taurate in a range from about 0.1% to about 8.0% by weight, sodium cocoyl isethionate in a range from about 0.1% to about 8.0% by weight, polyquaterium-10 in a range from about 0.05% to about 2.0% by weight, cetrimonium chloride in a range from about 0.1% to about 5.0% by weight, and the acrylates/C10-30 alkyl acrylate crosspolymer in a range from about 0.05% to about 2.0% by weight. All of the above weight percentages are based on the total weight of the composition.

According to an embodiment, the composition further comprising at least one amphoteric conditioning agent selected from the group consisting of polyquaternium-22, polyquaternium-39, polyquaternium-47 and polyquaternium-53.

According to another embodiment of the invention, a method of cleansing and conditioning hair includes the steps of (a) providing a composition for hair cleansing and conditioning having at least one anionic surfactant, at least one cationic hair conditioning agent, and an acrylate-based polymer capable of thickening and stabilizing the composition, such that the composition is essentially free of sulfate-based surfactant and silicone-based hair condition agent; (b) applying the composition to the hair of a user; and (c) rinsing the treated hair with sufficient amount of water.

In the following sections, certain compounds are further identified by the names according to the International Nomenclature of Cosmetic Ingredients (INCI) system.

DETAILED DESCRIPTION OF THE INVENTION

An embodiment of the invention is a composition for hair cleansing and conditioning that is essentially free of sulfate-based surfactants and silicone-based conditioning agents. The composition includes at least one anionic surfactant, at least one cationic hair conditioning agent and a thickening polymer capable of thickening and stabilizing the composition.

The term "hair cleansing", as used herein, means washing the hair with shampoo and water, so that dirt and oily materials are removed. "Hair cleansing" agents are surfactant molecules that are to be further elaborated below.

The term "hair conditioning", as used herein, means treating the hair with agents that impart to hair at least one property chosen from combability, manageability, moisture-retentivity, luster, shine and softness. "Hair conditioning" agents are to be further elaborated below.

"Hair conditioning" is usually carried out subsequent to "hair cleansing". Herein according to the present invention, "hair conditioning" occurs in conjunction with "hair cleansing".

The term "at least one", as used herein, means one or more and thus includes individual components as well as mixtures or combinations.

The terms "essentially free of sulfate-based surfactant" and "essentially sulfate free" refer to the contents of sulfate-based surfactants in the composition of the present invention. "Essentially free of sulfate-based surfactant" means that, while it prefers that no sulfate-based surfactants be present in the composition, it is possible to have very small amounts of sulfate-based surfactants in the composition of the invention, provided that these amounts do not materially affect the advantageous properties of the composition. In particular, "essentially free of sulfate-based surfactant" means that the sulfate-based surfactants can be present in the composition at an amount of less than about 2.0% by weight, typically less than about 1.5% by weight, typically less than about 1.0% by weight, typically less than about 0.5% by weight, typically less than about 0.1% by weight, and more typically 0% by weight, based on the total weight of the composition.

The term "sulfate-based surfactant" as used herein, also means "sulfate-containing surfactant". Thus, the term "essentially free of sulfate-based surfactant" also means "essentially free of sulfate-containing surfactant".

The terms "essentially free of silicone-based hair conditioning agent" and "essentially silicone free" refer to the contents of silicone-based hair conditioning agent in the composition of the present invention. "Essentially free of silicone-based hair conditioning agent" means that, while it prefers that no silicone-based hair conditioning agent be present in the composition, it is possible to have very small amounts of silicone-based hair conditioning agent in the composition of the invention, provided that these amounts do not materially affect the advantageous properties of the composition. In particular, "essentially free of silicone-based hair conditioning agent" means that the silicone-based hair conditioning agent can be present in the composition at an amount of less than about 2.0% by weight, typically less than about 1.5% by weight, typically less than about 1.0% by weight, typically less than about 0.5% by weight, typically less than about 0.1% by weight, and more typically 0% by weight, based on the total weight of the composition.

The term "silicone-based hair conditioning agent", as used herein, also means "silicon-containing hair condition agent". Thus, the term "essentially free of silicone-based hair conditioning agent" also means "essentially free of silicone-containing hair conditioning agent".

The term "stabilizing the composition" means that the formulation derived from the composition retains its initial appearance and specifications at various temperatures for a specific time period.

Hair cleansing agents in shampoo formulations are surfactant molecules that have a polar end and a non-polar end. The polar end of the surfactant molecule is hydrophilic because it attracts water molecules, while the non-polar end of the surfactant molecule is hydrophobic because it repels water molecules. At sufficient quantities in an aqueous environment, surfactant molecules organize themselves to form spherical structures called micelles, such that the polar ends appear on the outer surface (i.e., facing the water) while the non-polar ends appear inside. Surfactants enhance hair cleansing by attaching the non-polar ends of the surfactant molecules to oily materials on the hair and keeping them inside the micelles. Effectively, the oily materials are broken up by the non-polar ends of the surfactant molecules and stored inside the micelles, while the polar ends of the surfactant molecules keep the micelles soluble in water.

Surfactants may be anionic (negatively-charged), cationic (positively-charged), nonionic (not charged) or amphoteric (both negatively-charged and positively-charged). Examples of anionic surfactants are sulfates, sulfonates, phosphites, phosphates, phosphonates and the like. Examples of cationic surfactants are alkyl ammonium salts, quaternary ammonium salts and the like. Examples of nonionic surfactants are alkoxylated alcohols, alkoxylated phenols, fatty acid esters, amine derivatives, amide derivatives and the like. Examples of amphoteric surfactants are amino propionic acid derivatives, imido propionic acid derivatives, betaines, sulfobetaines, and the like.

Conventional hair cleansing agents contain surfactants such as sodium lauryl sulfate, sodium laureth sulfate, ammonium lauryl sulfate and ammonium laureth sulfate. These sulfate based surfactants are effective as surfactants for hair cleansing because they remove oily particles from hair efficiently. However, sulfate-based surfactants are less desirable because consumers consider them to be less mild.

According to an embodiment of the invention, the at least one anionic surfactant is essentially free of sulfate-based surfactant and is a member selected from the group consisting of an isethionate, a taurate, a sarcosinate, a sulfosuccinate, a sulfoacetate, a glycinate, a glutamate and a carboxylate, wherein the at least one anionic surfactant has an alkyl chain from $C_8$ to $C_{20}$, and a solubilizing counter cation selected from sodium, potassium and ammonium. Preferably, the at least one anionic surfactant is essentially free of sulfate-based surfactant and is a member selected from a taurate and an isethionate, wherein the at least one anionic surfactant has an alkyl chain from $C_8$ to $C_{20}$, and a solubilizing counter cation selected from sodium, potassium and ammonium.

According to an embodiment of the invention, the hair cleansing and conditioning composition comprises at least one anionic surfactant that is essentially free of sulfate-based surfactant. The at least one anionic surfactant can be one member selected from the group consisting of sodium methyl cocoyl taurate, sodium cocoyl isethionate, sodium lauryl methyl isethionate and sodium methyl oleoyl taurate.

The composition may also include two or more anionic surfactants that are essentially free of sulfate-based surfactant. The anionic surfactants can be two members selected from the group consisting of sodium methyl cocoyl taurate, sodium cocoyl isethionate, sodium lauryl methyl isethionate and sodium methyl oleoyl taurate.

According to an embodiment, the anionic surfactants suitable for the composition are sodium methyl cocoyl taurate and sodium cocoyl isethionate. Sodium methyl cocoyl taurate offers high lathering power, high foam stabilizing effect, good cleansing property and mildness. Sodium cocoyl isethionate also exhibits similar cleansing, lathering and foaming properties.

According to another embodiment of the invention, additional anionic surfactants may be adopted to be cleansing agents, including sodium lauryl methyl isethionate, sodium cocoyl glutamate and sodium methyl oleoyl taurate. In addition, non-ionic surfactant such as decyl glucoside may be used in addition to taurates and isethionates as part of the composition for hair cleansing and conditioning.

According to an embodiment, the anionic surfactant ranges from about 0.1% to about 16.0% by weight, preferably from about 0.5% to about 14.0% by weight, and more preferably from about 1.0% to about 12.0% by weight, based on the total weight of the composition.

According to an embodiment, the anionic surfactants are a taurate and an isethionate, wherein the taurate ranges from about 0.1% to about 8.0% by weight, and the isethionate ranges from about 0.1% to about 8.0% by weight, based on the total weight of the total composition.

Preferably, regarding the amounts of the anionic surfactants in the composition of the present invention, the taurate ranges from about 0.5% to about 7.0% by weight, and the isethionate ranges from about 0.5% to about 7.0% by weight, based on the total weight of the total composition.

More preferably, regarding the amounts of the anionic surfactants in the composition of the present invention, the taurate ranges from about 1.0% to about 6.0% by weight, and the isethionate ranges from about 1.0% to about 6.0% by weight, based on the total weight of the total composition.

Hair conditioning agents protect the hair by forming a coat on the outer layer of the hair shaft called cuticle. Conditioning agents mimic the function of sebum, the natural conditioner that is produced and secreted by the sebaceous gland of the hair follicle. Sebum, which is a mixture of wax monoesters, triglycerides, fatty acids and squalene, binds with keratin, the protein of the hair shaft. Because keratin is usually anionic (negatively-charged), conditioning agents that are cationic (positively charged) would work well in binding with keratin.

Hair conditioners may be categorized by the purposes they are intended to achieve for the consumer, such as moisturizing conditioners, protein conditioners or static-reducing conditioners. For hair that is dry, curly and coarse, moisturizing conditioners that use alcohols, silicones and essential oils will be helpful. For hair that needs to look fuller, protein conditioners that help to coat the hair shaft will be helpful. For hair that is tangled and unmanageable due to scales of the cuticle layer of the hair shaft being flaky, static-reducing conditioners helps the scales lay flat on the hair shaft, and thus allow each hair to be separated and manageable.

Silicone-based hair conditioners have been popular because they tend to make hair look full and manageable to the consumer. Silicone-based hair conditioners provide the hair with a smooth silky feel, shine, moisture and superior combing benefits. However, upon prolonged use, silicone-based hair conditioners have a tendency to attract dirt, which reduces the shine and the overall appearance of the hair. Silicone-based hair conditioning agents also have the tendency to build up upon prolonged usage, which weighs the hair down and could leave an unpleasant residue on the hair fibers. Therefore, depending on the consumer's preference, silicone-based conditioning agents may be less desirable.

According to an embodiment of the invention, the composition for hair cleansing and conditioning also includes at least one cationic hair conditioning agent that is essentially free of silicone-based hair conditioning agent. The composition may also include two or more cationic hair conditioning agents that are essentially free of silicone-based hair conditioning agent. Cationic hair conditioning agents suitable for the composition of the invention are Polyquaterium-10 (also called quaternized polyhydroxyethyl cellulose) and cetrimonium chloride (also called cetyl trimethyl ammonium chloride, CTAC). Polyquaterium-10 is a cationic and multifunctioning polymer that improves compatibility with moisture and contributes to the appearance of fullness. Cetrimonium chloride, being positively-charged, binds well with the protein keratin on the hair and thus helps to prevent the build-up of static electricity.

According to another embodiment of the invention, the composition for hair cleansing and conditioning includes other cationic hair conditioning agents such as behentrimonium chloride (also known as docosyl trimethyl ammonium chloride), behentrimonium methosulfate, steartrimonium chloride, stearalkonium chloride and dicetyldimonium chloride.

In addition, the at least one cationic conditioning agent can be an amphoteric conditioning agent that can carry a cationic charge based on pH, or an amphoteric conditioning agent that remains amphoteric and provides conditioning attributes to the hair. Examples of amphoteric conditioning agents include: polyquaternium-22, polyquaternium-39, polyquaternium-47, and polyquaternium-53.

According to an embodiment, the composition further comprising at least one amphoteric conditioning agent selected from the group consisting of polyquaternium-22, polyquaternium-39, polyquaternium-47 and polyquaternium-53.

According to an embodiment of the invention, the at least one cationic conditioning agent of the composition can be combined with at least one amphoteric conditioning agent as a mixture. The use of the at least one amphoteric conditioning agent as part of a combination with the at least one cationic conditioning agent results in compositions that exhibit different attributes.

Additional conditioning agents that can work in conjunction with the cationic conditioning agents listed above include, but not limited to, four different types: (A) amphoteric conditioning agents, (B) cationic conditioning agents, (C) non-ionic conditioning agents, and (D) anionic conditioning agents. Examples of each type are listed below.

(A) Amphoteric conditioning agents: arginine, asparagines, aspartic acid, glycine, glutamic acid, lysine, methionine, phenylalanine, serine, threonine, tyrosine, tryptophan, valine, gelatin, Quaternium-27, oleamidopropyl betaine, disodium cocoamphodiacetate, disodium cocoamphodipropionate, disodium lauroamphodiacetate, sodium cocoamphopropionate, sodium cocoamphoacetate, meadowfoam delta lactone, cocoamidopropyl betaine, cocoamidopropyl hydroxysultaine, lauramidopropyl betaine, carnitine, hydroxyproline, acetyl hydroxy proline, isoleucine, lauroyl lysine, lauroyl sarcosine, polylysine, proline, rice amino acids, silk amino acids, wheat amino acids and mixture thereof;

(B) Cationic conditioning agents: hydroxypropyltrimonium chloride, cocotrimonium methosulfate, olealkonium chloride, steartrimonium chloride, babassuamidopropalkonium chloride, brassicamidopropyl dimethylamine, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, dilinoleamidopropyl dimethylamine dimethicone PEG-7 phosphate and mixture thereof;

(C) Non-ionic conditioning agents: petrolatum, mineral oil, lanolin oil, *cocas nucifera* (coconut) oil, *Olea Europea* (Olive) fruit oil, *Simmondsia Chinensis* (Jojoba) seed oil, *Prunus Armeniaca* (Apricot) kernel oil, *Crambe Abyssinica* seed oil, vegetable oil, *Zea Mays* (Corn) oil, caprylyl glycol, cetyl glycol, glycerin, sarcosine, hydroxypropyl guar, cocamide MIPA, cyclomethicone, dimethicone, $C_{26-28}$ alkyl dimethicone, Polysilicone-13, acetylated lanolin alcohol, cetearyl isononanoate, cetearyl ethylhexanoate, Triethylhexanoin, phytantriol, PPG-5 Butyl Ether, coco-betaine, acetamide MEA, behenamide MEA, linoleamide DEA, linolenic acid, maltodextrin, squalane, squalene, *Salix Alba* (Willow) bark extract, *Morus Alba* (Mulberry) leaf, phenyltrimethicone, hexyl dimethicone, capric/caprylic triglyceride, cetearyl palmitate, hydrogenated olive oil hexyl esters, *Ginkgo Biloba* nut extract, inositol, Dimethicone Beeswax, PEG-8 dimethicone, PPG-12 dimethicone, panthenol, methanediol, ceramide 3, Phytosphingosine, salicylic acid, linoleamide MEA, linoleamide MIPA, niacin, thiodiglycoamide, hydrolyzed soy protein, hydrolyzed oat protein, hydrolyzed rice protein, hydrolyzed vegetable protein, hydrolyzed yeast protein, casein, collagen, procollagen, keratin, glycoproteins, hydrolyzed wheat protein and mixture thereof; and (D) Anionic conditioning agents: sodium glutamate, potassium cocoyl glutamate, cocoyl sarcosine, histidine, sodium lauroyl glutamate, stearoyl sarcosine, whey protein, methyl cocoate, sodium cocoate, linoleic acid and mixture thereof.

According to an embodiment, the at least one cationic conditioning agent is a member selected from the group consisting of polyquaterium-10, cetrimonium chloride, behentrimonium chloride, behentrimonium methosulfate, steartrimonium chloride, stearalkonium chloride and dicetyldimonium chloride.

According to an embodiment, the cationic conditioning agents are two members selected from the group consisting of polyquaterium-10, cetrimonium chloride, behentrimonium chloride, behentrimonium methosulfate, steartrimonium chloride, stearalkonium chloride and dicetyldimonium chloride.

According to an embodiment, the cationic conditioning agent are polyquaterium-10, and at least one additional cationic hair conditioning agent selected from the group consisting of behentrimonium chloride, behentrimonium methosulfate, steartrimonium chloride, stearalkonium chloride and dicetyldimonium chloride.

According to an embodiment of the invention, the cationic conditioning agents are polyquaterium-10 and cetrimonium chloride.

According to an embodiment, the cationic hair conditioning agent ranges from about 0.05% to about 7.0% by weight, preferably from about 0.1% to about 5.5% by weight, and more preferably from about 0.2% to about 4.0% by weight, based on the total weight of the composition.

According to an embodiment, regarding the amounts of the cationic hair conditioning agents, polyquaterium-10 ranges from about 0.05% to about 2.0% by weight, and the at least one additional cationic hair conditioning agent ranges from about 0.1% to about 5.0% by weight, wherein the weight percentages are based on the total weight of the composition.

Preferably, regarding the amounts of the cationic hair conditioning agents, polyquaterium-10 ranges from about 0.1% to about 1.5% by weight, and the at least one additional cationic hair conditioning agent ranges from about 0.25% to about 4.0% by weight, wherein the weight percentages are based on the total weight of the composition.

More preferably, regarding the amounts of the cationic hair conditioning agents, polyquaterium-10 ranges from about 0.2% to about 1.0% by weight, and the at least one additional cationic hair conditioning agent ranges from about 0.4% to about 3.0% by weight, wherein the weight percentages are based on the total weight of the composition.

An acrylate-based polymer capable of thickening the composition is helpful to provide stabilization of the composition, and thus yielding favorable properties to the hair cleansing and conditioning composition. The hair cleansing and conditioning composition of the present invention can have a range of appearances from a lotion, to a gel or a cream. A lotion consistency is preferred for easier distribution during application, allowing the consumer to cleanse and condition the entire length of the hair fiber evenly from root to ends.

The acrylate-based polymer can be a copolymer or a crosspolymer. One type of an acrylate-based polymer is known by the INCI name "acrylates/C10-30 alkyl acrylate crosspolymer". Additional examples of the acrylate-based polymer include, but not limited to, polyacrylate-1 crosspolymer, carbomer, acrylates/acrylamide copolymer and acrylate copolymer.

According to an embodiment, the acrylate-based polymer capable of thickening and stabilizing the composition is an acrylates/C10-30 alkyl acrylate crosspolymer.

According to an embodiment, the acrylate-based polymer ranges from about 0.05% to about 2.0% by weight, preferably from 0.1% to about 1.5% by weight, and more preferably from 0.2% to about 1.0% by weight, based on the total weight of the composition.

According to an embodiment, the acrylates/C10-30 alkyl acrylate crosspolymer ranges from about 0.05% to about 2.0% by weight, preferably from about 0.1% to about 1.5% by weight, and more preferably from about 0.2% to about 1.0% by weight, based on the total weight of the composition.

The various components of the composition of the present invention can be selected accordingly: the anionic surfactants are sodium methyl taurate and sodium cocoyl isethionate, the cationic conditioning agents are polyquaterium-10 and cetrimonium chloride, and the acrylate-based polymer capable of thickening and stabilizing the composition is an acrylates/C10-30 alkyl acrylate crosspolymer.

According to an embodiment, the at least one anionic surfactant ranges from about 0.1% to about 16% by weight, the at least one cationic hair conditioning agent ranges from about 0.05% to about 7.0% by weight, and the acrylate-based polymer ranges from 0.05% to about 2.0% by weight, wherein the weight percentages are based on the total weight of the composition.

According to an embodiment, the composition comprises sodium methyl cocoyl taurate in a range from about 0.1% to about 8.0% by weight, sodium cocoyl isethionate in a range from about 0.1% to about 8.0% by weight, polyquaterium-10 M a range from about 0.05% to about 2.0% by weight, cetrimonium chloride in a range from about 0.1% to about 5.0% by weight, and the acrylates/C10-30 alkyl acrylate crosspolymer in a range from about 0.05% to about 2.0% by weight. All of the above weight percentages are based on the total weight of the composition.

The composition according to the invention leads to several favorable characteristics, including maintaining foam structure, foam stability and foaming, while achieving cleansing and conditioning properties. The composition provides a very unique balance between cleansing and conditioning. The anionic surfactants that are essentially free of sulfate-based surfactant according to the composition are able to cleanse the hair of sebum, styling product build-up. Also, the cationic hair conditioners that are essentially free of silicone-based conditioning agents are able to form a deposit on the surface of the hair cuticle, resulting in hair that is smooth and conditioned. The composition has shown excellent cosmetic properties such as curl definition and superior frizz control without weighing the hair down, which is a very desirable attribute that the consumers prefer. As a result, the composition according to the invention achieves the goal of hair cleansing in conjunction with the goal of hair conditioning.

In the composition of the present invention, the combination of anionic surfactants such as sodium methyl cocoyl taurate and sodium cocoyl isethionate with cationic hair conditioning agents such as Polyquaterium-10 ("PQ-10") and cetyl trimethyl ammonium chloride ("CTAC") cleanse the hair while leaving it conditioned and smooth. In addition, the composition has unique flow properties due to the presence of the acrylate-based polymer and the anionic surfactant sodium cocoyl isethionate, thus providing good foaming attributes. Furthermore, the acrylate-based polymer also stabilizes and optimizes the surfactant system. According to the invention, the preferred hair cleansing and conditioning composition has a consistency of a lotion, which allows for easy distribution throughout the hair and contributes to a quick flash foam and easy detangling.

In some embodiments of the present invention, anionic surfactant sodium lauryl methyl isethionate may be used instead of sodium cocoyl isethionate. Further, cationic conditioner behentrimonium chloride (docosyl trimethyl ammonium chloride) and/or behentrimonium methosulfate may substitute for cetrimonium chloride. In other cases, any combination of Polyquaterium-10, cetrimonium chloride, behentrimonium chloride and behentrimonium methosulfate may be used for the present invention, resulting in different foam properties.

According to another embodiment, a composition for hair cleansing and conditioning, comprising: sodium methyl cocoyl taurate, sodium cocoyl isethionate, polyquaterium-10, cetrimonium chloride and an acrylates/C10-30 alkyl acrylate crosspolymer, wherein the composition is essentially free of sulfate-based surfactant and silicone-based hair conditioning agent, sodium methyl cocoyl taurate ranges from about 0.1% to about 8.0% by weight, sodium cocoyl isethionate ranges from about 0.1% to about 8.0% by weight, polyquaterium-10 ranges from about 0.05% to about 2.0% by weight, cetrimonium chloride ranges from about 0.1% to about 5.0% by weight, and the acrylates/C10-30 alkyl acrylate crosspolymer ranges from about 0.05% to about 2.0% by weight, and the weight percentages are based on the total weight of the composition.

According to another embodiment of the invention, a method of cleansing and conditioning hair includes the steps of (a) providing a composition for hair cleansing and conditioning having at least one anionic surfactant, at least one cationic hair conditioning agent, and an acrylate-based polymer capable of thickening and stabilizing the composition, such that the composition is essentially free of sulfate-based surfactant and silicone-based hair conditioning agent; (b) applying the composition to the hair of a user; and (c) rinsing the treated hair with sufficient amount of water.

The invention is illustrated in greater detail in the following examples, which are exemplary and not limiting. The amounts are given as weight percentages relative to the total weight of the composition.

Example 1

Different Formulations of the Invention

Different formulations of the present invention are presented herein as an illustration of the various cleansing and conditioning compositions. All of the numbers in the table below are percent by weight active, based on the total weight of the composition.

| INCI Name of Component | Formulations | | | | | | |
|---|---|---|---|---|---|---|---|
| | 1 | 2 | 3 | 4 | 5 | 6 | 7 |
| ACRYLATES/C10-30 ALKYL ACRYLATE CROSSPOLYMER | 0.45 | 0.45 | 0.45 | 0.45 | 0.45 | 0.45 | 0.45 |
| SODIUM LAUROYL METHYL ISETHIONATE | | 3.5175 | | | 1.14 | | |
| CETRIMONIUM CHLORIDE | 0.625 | 0.625 | 0.625 | 0.625 | 0.625 | 0.625 | 0.625 |
| DECYL GLUCOSE | | | | 0.795 | 0.795 | | |
| SODIUM COCOYL ISETHIONATE | 3.52 | | 2.992 | 2.992 | 2.0064 | 3.52 | 3.52 |
| SODIUM METHYL COCOYL TAURATE | 3 | 3 | 3.51 | 3.51 | 3.51 | 3 | 3 |
| POLYQUATERNIUM-10 | 0.4 | 0.4 | 0.4 | 0.4 | 0.4 | 0.4 | 0.4 |
| POLYQUATERNIUM-53 | | | | | | 0.2 | |
| POLYQUATERNIUM-22 | | | | | | | 0.3 |
| WATER | QS TO 100 | QS TO 100 | QS TO 100 | QS TO 100 | QS TO 100 | QS TO 100 | QS TO 100 |

Example 2

Comparison Between a Formulation of the Invention and a Sulfate Free Shampoo A comparison is performed between a formulation of the invention and a sample based on a sulfate free cleansing composition that contains taurates, polyquaternium-10 and an amphoteric surfactant. In this comparison, each attribute is evaluated by trained experts, using a total of eight (8) models for each test. The attributes are evaluated on a scale as indicated below, and a numerical value is assigned to the tested sample. A smaller number indicates a lesser degree of satisfaction, while a larger number indicates a greater degree of satisfaction under the tested attribute.

The significance of the difference of the numerical values of each attribute between the invention and a comparative sample is considered as:

(1) No difference, if the numerical values are different by less than 0.5;

(2) Small difference if the numerical values are different by 0.5 to less than 1.0;

(3) Noticeable difference, if the numerical values are different by 1.0 to less than 1.5; and (4) Dramatic difference, if the numerical values are different by 1.5 or greater.

The formulation according to the invention includes cetrimonium chloride and sodium cocoyl isethionate, while the sulfate-free shampoo does not. According to the comparative study, the invention exhibits advantages over the sulfate-free shampoo in discipline and visual effects on smooth hair.

Example 3

Comparison Between a Formulation of the Invention and a Comparative Sulfate Free Composition A comparison is performed between a formulation of the invention and a comparative composition that is similar to the invention, except the use of an amphoteric surfactant and a cationic conditioning agent. In this comparison, each attribute is evaluated by trained experts, using a total of eight (8) models for each test. The attributes are evaluated on a scale of "0" to "5" as indicated below, and a numerical value is assigned to the tested sample. A value of "0" indicates an unsatisfactory test result, while a value of "5" indicates a fully satisfactory rest result.

The significance of the difference of the numerical values of each attribute between the invention and a comparative sample is considered as:

(1) No difference, if the numerical values are different by less than 0.5;

(2) Small difference, if the numerical values are different by 0.5 to less than 1.0;

| Attributes | A Formulation of the Invention | A Sulfate Free Shampoo | Difference in Numerical Values of Attribute | Significance of Difference |
|---|---|---|---|---|
| Flash Foam (1st) (0-5) | 1.75 | 3.13 | 1.38 | Noticeable |
| Distribution Ease (0-5) | 2.56 | 3.38 | 0.82 | Small |
| Abundance of Foam (1st) (0-5) | 1.88 | 3.25 | 1.37 | Noticeable |
| Airy Foam (1st) (1-4) | 2.25 | 3.13 | 0.88 | Small |
| Foam Stability (1st) (1-4) | 2.13 | 3.00 | 0.87 | Small |
| Hair Smoothness in Foam (1st) (1-4) | 3.00 | 2.63 | 0.37 | No Difference |
| Degree of Frizz (1-4) | 1.25 | 1.50 | 0.25 | No Difference |
| Discipline (1-4) | 3.75 | 3.00 | 0.75 | Small |
| Shine (1-6) | 3.50 | 3.38 | 0.12 | No Difference |
| Smooth Hair (visual) (0-5) | 3.31 | 2.50 | 0.81 | Small |
| Smooth Hair (feel) (0-5) | 2.69 | 2.31 | 0.38 | No Difference |
| Static Flyaway (0-5) | 0.13 | 0.50 | 0.37 | No Difference |

(3) Noticeable difference, if the numerical values are different by 1.0 to less than 1.5; and (4) Dramatic difference, if the numerical values are different by 1.5 or greater.

| Attributes | A Formulation of the Invention | A Comparative Sulfate Free Composition | Difference in Numerical Values of Attribute | Significance of Difference |
|---|---|---|---|---|
| Flash Foam (0-5) | 2.75 | 1.50 | 1.25 | Noticeable |
| Abundant Foam (0-5) | 2.50 | 1.69 | 0.81 | No difference |
| Squeaky Clean (0-5) | 1.50 | 1.25 | 0.25 | No difference |
| Wet Hair Combing (0-5) | 3.00 | 3.50 | 0.50 | Small |
| Wet Hair Smoothness (0-5) | 3.19 | 3.13 | 0.06 | No difference |
| Body (0-5) | 2.69 | 2.13 | 0.56 | Small |
| Dry Hair Suppleness (0-5) | 3.00 | 3.25 | 0.25 | No difference |
| Smoothness (visual) (0-5) | 2.69 | 2.88 | 0.19 | No difference |
| Smoothness (tactile) (0-5) | 2.75 | 3.19 | 0.44 | No difference |
| Static Fly Away (0-5) | 0.31 | 0.31 | 0.00 | No difference |

The formulation according to the invention includes the use of anionic surfactants while the comparative sulfate free composition uses an amphoteric surfactant. According to the comparative study, the invention exhibits advantages over the comparative sulfate-free shampoo in attributes such as flash foam and body.

Example 4

Comparison Between a Formulation of the Invention and Deva Curl No Poo™ Shampoo

A comparison is performed between a formulation of the invention and the Deva Curl No Poo™ shampoo. In this comparison, each attribute is evaluated by trained experts, using a total of eight (8) models for each test. The attributes are evaluated on a scale as indicated below, and a numerical value is assigned to the tested sample. A smaller number indicates a lesser degree of satisfaction, while a larger number indicates a greater degree of satisfaction under the tested attribute.

The significance of the difference of the numerical values of each attribute between the invention and a comparative sample is considered as:

(1) No difference, if the numerical values are different by less than 0.5;

(2) Small difference, if the numerical values are different by 0.5 to less than 1.0;

(3) Noticeable difference, if the numerical values are different by 1.0 to less than 1.5; and (4) Dramatic difference, if the numerical values are different by 1.5 or greater.

| Attributes | A Formulation of the Invention | Deva Curl No Poo ™ Shampoo | Difference in Numerical Values of Attribute | Significance of Difference |
|---|---|---|---|---|
| Melt Sensation (hand) (0-5) | 1.13 | 1.75 | 0.62 | Small |
| Distribution thru Ends (1.4) | 3.25 | 2.63 | 0.62 | Small |
| Detangling in Product (1-4) | 2.88 | 2.50 | 0.38 | No difference |
| Supple in Product (0-5) | 2.75 | 2.31 | 0.44 | No difference |
| Sticky (1-4) | 2.25 | 1.88 | 0.37 | No difference |
| Rinse Speed (0-5) | 1.94 | 2.63 | 0.69 | Small |
| Smooth Hair Feel (rinsing) (0-5) | 3.38 | 2.69 | 0.69 | Small |
| Wet Hair Smoothness (0-5) | 3.19 | 2.50 | 0.69 | Small |
| Hair Dries Quickly (0-4) | 1.63 | 1.88 | 0.25 | No difference |
| Dry Hair Combing (0-5) | 3.31 | 2.75 | 0.56 | Small |
| Shine (0-5) | 3.25 | 2.56 | 0.69 | Small |
| Smoothness (visual) (0-5) | 3.06 | 2.38 | 0.68 | Small |
| Smoothness (tactile) (0-5) | 3.06 | 2.38 | 0.68 | Small |

The invention includes cetrimonium chloride and Polyquaternium-10, while the Deva Curl No Poo™ contains Behentrimonium chloride and Polyquaternium-7 cationic conditioning agents. According to the comparative study, the invention exhibits advantages over the Deva Curl No Poo™ Shampoo in attributes such as distribution through ends, smooth hair feel during rinsing, wet hair smoothness, dry hair combing, shine, visual and tactile smoothness.

Example 5

Comparison Between a Formulation of the Invention and a Classical Sulfate-Based Shampoo Composition A comparison is performed between a formulation of the invention and a sample of a classical sulfate-based shampoo composition. In this comparison, each attribute is evaluated by trained experts, using a total of eight (8) models for each test. The attributes are evaluated on a scale of "0" to "5" as indicated below, and a numerical value is assigned to the tested sample. A value of "0" indicates an unsatisfactory test result, while a value of "5" indicates a fully satisfactory rest result.

The significance of the difference of the numerical values of each attribute between the invention and a comparative sample is considered as:

(1) No difference, if the numerical values are different by less than 0.5;

(2) Small difference, if the numerical values are different by 0.5 to less than 1.0;

(3) Noticeable difference, if the numerical values are different by 1.0 to less than 1.5; and (4) Dramatic difference, if the numerical values are different by 1.5 or greater.

The attribute "discipline" means that hair easily takes on the shape which was given during the drying process. The attribute "with shape" means that the hair has a nice curl and shape without the addition of styling products.

| Attributes | A Formulation of the Invention | A Sulfate-Based Shampoo | Difference in Numerical Values of Attribute | Significance of Difference |
|---|---|---|---|---|
| Flash Foam (0-5) | 1.69 | 2.94 | 1.25 | Noticeable |
| Airy Foam (0-5) | 1.63 | 2.81 | 1.18 | Noticeable |
| Abundant Foam (0-5) | 1.81 | 3.44 | 1.63 | Dramatic |
| Smooth Hair Feel in Lather (0-5) | 3.38 | 2.38 | 1.00 | Noticeable |
| (Rinsing) Suppleness (0-5) | 2.81 | 2.13 | 0.68 | Small |
| Squeaky Clean (0-5) | 0.69 | 2.00 | 1.31 | Noticeable |
| Wet Hair Combing (0-5) | 3.50 | 2.63 | 0.87 | Small |
| Light Hair (0-5) | 1.75 | 2.63 | 0.88 | Small |
| Wet Hair Smoothness (0-5) | 3.31 | 2.00 | 1.31 | Noticeable |
| (Amount) Coating (0-5) | 2.75 | 1.44 | 1.31 | Noticeable |
| Discipline (1-4) | 3.13 | 1.88 | 1.25 | Noticeable |
| With Shape (1-4) | 3.00 | 2.38 | 0.62 | Small |
| Shine (0-5) | 3.06 | 2.38 | 0.68 | Small |
| Smoothness (visual) (0-5) | 2.69 | 1.63 | 1.06 | Noticeable |
| Smoothness (tactile) (0-5) | 2.69 | 2.13 | 0.56 | Small |

The invention includes the sulfate-free anionic surfactants, while the Classical Sulfate-Based Shampoo does not. According to the comparative study, the invention exhibits advantages over the Classical Sulfate-Based Shampoo in attributes such as smooth hair feel in lather, rinsing suppleness, wet hair combing, wet hair smoothness, the amount of coating, discipline, shape, shine, visual and tactile smoothness.

Example 6

Comparison Between a Formulation of the Invention and a Traditional Sulfate-Based Shampoo/Conditioner Regimen A comparison is performed between a formulation of the invention and a sample of a traditional sulfate-based Shampoo/Conditioner Regimen. In this comparison, each attribute is evaluated by trained experts, using a total of eight (8) models for each test. The attributes are evaluated on a scale of "0" to "5" as indicated below, and a numerical value is assigned to the tested sample. A value of "0" indicates an unsatisfactory test result, while a value of "5" indicates a fully satisfactory rest result.

The significance of the difference of the numerical values of each attribute between the invention and a comparative sample is considered as:

(1) No difference, if the numerical values are different by less than 0.5;

(2) Small difference, if the numerical values are different by 0.5 to less than 1.0;

(3) Noticeable difference, if the numerical values are different by 1.0 to less than 1.5; and (4) Dramatic difference, if the numerical values are different by 1.5 or greater.

| Attributes | A Formulation of the Invention | A Shampoo/ Conditioner Regimen | Difference in Numerical Values of Attribute | Significance of Difference |
|---|---|---|---|---|
| Flash Foam (0-5) | 2.75 | 2.25 | 0.50 | Small |
| Airy Foam (0-5) | 1.69 | 2.19 | 0.50 | Small |
| Abundant Foam (0-5) | 2.06 | 2.50 | 0.44 | No Difference |
| Hold/Lather Stability (0-5) | 2.75 | 3.06 | 0.31 | No Difference |
| Rinsing Speed (0-5) | 2.38 | 2.94 | 0.56 | Small |
| Squeaky Clean (0-5) | 0.81 | 1.50 | 0.69 | Small |
| Wet Hair Combing (0-5) | 3.25 | 2.75 | 0.50 | Small |
| Root Lift (0-5) | 1.50 | 2.38 | 0.88 | Small |
| (Amount) Coating (0-5) | 2.63 | 1.75 | 0.88 | Small |
| Dry Hair Suppleness (0-5) | 2.50 | 2.00 | 0.50 | Small |
| Dry Hair Combing (0-5) | 2.69 | 2.69 | 0.00 | No Difference |
| Shine (0-5) | 2.56 | 2.81 | 0.25 | No Difference |

The invention includes the sulfate-free anionic surfactants, while the Traditional Sulfate-Based Shampoo/Conditioner Regimen does not. According to the comparative study, the invention exhibits advantages over the Traditional Sulfate-Based Shampoo/Conditioner Regimen in attributes such as flash foam, wet hair combing, amount coating and dry hair suppleness.

The present invention of a hair cleansing and conditioning composition and the method of using the same have achieved several desirable advantages from the perspective of the consumers. The inclusion of the cationic hair conditioning agents in the composition of the invention contributes to attributes such as discipline and visual effects on smooth hair as illustrated in the comparison of attributes in Example 2. Similarly, according the comparison of attributes in Example 4, the use of cetrimonium chloride and polyquaternium-10 in the invention enhances the attributes of smooth hair feel, wet hair smoothness, shine, as well as visual and tactile smoothness. The use of anionic surfactants rather than amphoteric surfactants resulted in better flash foam and body, as supported by the comparison of attributes in Example 3. The effects of sulfate-free anionic surfactant in the composition of the invention are manifested in the comparisons in Example 5, in which numerous advantages in smoothness, discipline, shape, shine, as well as visual and tactile smoothness. According to Example 6, the formulation of the invention, when compared with a traditional sulfate-based shampoo/conditioner regimen, exhibited advantageous attributes such as flash foam, wet hair combing, the amount of coating and dry hair suppleness. Therefore, the invention has achieved a hair cleansing and conditioning composition that is essentially free of sulfate-based surfactant and silicone-based hair conditioning agent while achieving a balance between cleansing and conditioning.

What is claimed is:

1. A composition for hair cleansing and conditioning, comprising: sodium methyl cocoyl taurate, sodium cocoyl isethionate, polyquaterium-10, cetrimonium chloride and an acrylates/C10-30 alkyl acrylate crosspolymer, wherein
    the composition is essentially free of sulfate-based surfactant and silicone-based hair conditioning agent,
    sodium methyl cocoyl taurate ranges from about 0.1% to about 8.0% by weight, sodium cocoyl isethionate ranges from about 0.1% to about 8.0% by weight, polyquaterium-10 ranges from about 0.05% to about 2.0% by weight, cetrimonium chloride ranges from about 0.1% to about 5.0% by weight, and the acrylates/C10-30 alkyl acrylate crosspolymer ranges from about 0.05% to about 2.0% by weight, and
    the weight percentages are based on the total weight of the composition.

2. The composition according to claim 1, further comprising at least one amphoteric conditioning agent selected from the group consisting of polyquaternium-22, polyquaternium-39, polyquaternium-47 and polyquaternium-53.

3. A method of cleansing and conditioning hair, comprising:
    (b) applying the composition according to claim 1 to treat the hair of a user; and
    (c) rinsing the treated hair with sufficient amount of water.

* * * * *